United States Patent [19]

O'Rourke

[11] Patent Number: 5,545,160

[45] Date of Patent: Aug. 13, 1996

[54] COMPUTER ORIENTED STEREOTACTIC MICRONEUROLOGICAL SURGERY

[76] Inventor: Daniel K. O'Rourke, 318 Carmen Dr., Collegeville, Pa. 19426

[21] Appl. No.: 566,822

[22] Filed: Aug. 14, 1990

[51] Int. Cl.$^6$ ..................................... A61B 5/06
[52] U.S. Cl. ................... 606/10; 606/2; 606/14; 356/12; 356/18; 356/375
[58] Field of Search ................ 606/2–5, 10–18, 606/130; 128/395–398; 356/1, 12, 18, 149, 375; 219/121.78, 121.82; 607/89

[56] References Cited

U.S. PATENT DOCUMENTS

| | | | |
|---|---|---|---|
| 3,696,248 | 10/1972 | Cunningham et al. | 250/203 R |
| 4,091,814 | 5/1978 | Togo | 606/18 |
| 4,164,222 | 8/1979 | Prokhorov et al. | 606/6 |
| 4,330,208 | 5/1982 | Eloy | 356/318 |
| 4,561,436 | 12/1985 | Munnerlyn | 606/4 |
| 4,573,797 | 3/1986 | Burns et al. | 356/350 |
| 4,651,732 | 3/1987 | Frederick | 606/130 |
| 4,722,601 | 2/1988 | McFarlane | 356/152 |
| 4,888,490 | 12/1989 | Bass et al. | 250/561 |
| 4,896,343 | 1/1990 | Saunders | 378/95 |
| 5,078,140 | 1/1992 | Kwoh | 606/130 |

FOREIGN PATENT DOCUMENTS 0824107 4/1981 U.S.S.R. .
2094590 9/1982 United Kingdom .................. 606/130

OTHER PUBLICATIONS

Reinhardt et al., "Interactive Sonar–Operated Device for Stereotactic and Open Surgery", Stereotac. Funct. Nerosurg, pp. 393–397 (Switzerland 1990).
Roberts et al., "The Stereotactic Operating Microscope: . . . ", ACTA Neurochirurgica, pp. 112–114 (U.S.A. 1989).
Reinhardt et al., "CT–Guided 'Real Time' Sterotaxy", ACTA Neurochirurgica, pp. 107–108 (Switzerland 1989).
Watanabe et al., "Open Surgery Assisted by the Neuronavigator . . . ", Neurosurgery, pp. 792–800 (U.S.A. 1991).

Primary Examiner—David M. Shay
Attorney, Agent, or Firm—James Creighton Wray

[57] ABSTRACT

An operating microscope has extensions on which are mounted neon lasers which focus beams through the focal point on the optical axis of the operating microscope. The beams produce two spots on an object when the object is away from the focal point, and a single spot on an object at a the focal point. Lightweight laser ring gyroscopes are connected to the operating microscope to determine spatial changes in the position and direction of the operating microscope and the focal point of the microscope.

16 Claims, 2 Drawing Sheets

5,545,160

COMPUTER ORIENTED STEREOTACTIC MICRONEUROLOGICAL SURGERY

BACKGROUND OF THE INVENTION

Developments in non invasive scanning of objects such as living tissue, and particularly brain tissues, permit precise information on hidden structures and contents. That is particularly true of the brain. Using available scanning techniques, a complete topography of the brain may be constructed and stored in a computer. Surgery, and particularly neurological surgery of the brain, are often preceded by precise topographical reconstruction of body parts on computer displays.

Using those reconstructions, a surgeon opens a body portion and conducts procedures, using at times an optical microscope and hand-directed instruments for conducting procedures.

In the case of neurological surgery in the brain, object areas must be accessed through controlled pathways to avoid undue injury or loss of function.

The present invention is directed to solving problems of coordinating the positioning of focal points of operating instruments with precise predetermined positions, especially locations identified by preliminary non invasive scanning techniques.

SUMMARY OF THE INVENTION

This invention aids neurosurgeons in brain surgery with the use of an integrated system of new and existing instruments. The purpose of the system is to allow a neurosurgeon to know where the focal point of an operating microscope is in three dimensions at any time. The integration of this knowledge with the use of available stereotaxic frame systems allows the correlation of imaging modalities at the points of interest. The invention is designed to provide a system simple to use, and one that is highly accurate. The basic system permits rapid expansion to allow for more advanced correlating modalities.

Recent technological advances in gyroscopes, chiefly for aviation and defense purposes, have produced highly reliable, compact and lightweight gyroscopes known as laser ring gyros (LRG). Those advanced gyroscopes work by measuring the doppler shift of a monochromatic laser beam which is reflected around a ring. Since movements of the apparatus produce doppler shifts of the beams, they make ideal gyroscopes. Further, because of this technology, gyroscopes can be produced in very small sizes, the smallest being the size of a microchip.

This invention involves several different points.

The weight of the apparatus and the size must not be so great that they will overcome the utility of the support for the operating microscope. This limits the total on scope system weight to less than 5 to 10 pounds.

The accuracy necessary presents a geometric problem which can be solved.

Because the focal point of the microscope is far away from the gyroscope, movements of the gyro must be interpreted in terms of the focal point of the scope.

The cost of the system must not be so great that its wide use is precluded.

An output link interprets the data generated by the gyro.

The focal point of the microscope must be readily apparent to the operator at any time that he wishes to use the system.

The selection of the gyroscope provides a lightweight, low cost, accurate instrument.

The degree of accuracy necessary is well within the limits of the available hardware.

The invention provides a geometric solution to the problem of the separation of the focal point of the LRG and the focal point of the scope. This is only one possible solution. Another is to purchase an LRG that displays not only its three dimensional point position, but also its angle to target. These types of gyroscopes may be more expensive; their selection will be contingent upon cost and accuracy. Another method of solving the problem is to have two gyros. That also affords a check, assuring the reliability of the position output data. Cost, weight and accuracy are taken into account.

An output link for the gyros displays the exact position of the focal point. An LED readout allows for the manual calculation of the focal point with the aid of a calculator-size computer. Sophistication may be increased to incorporate the use of heads-up displays or three dimensional hologram position modeling. The position of the focal point could be plotted against the skull (a fixed structure) and the brain to check for slack and movement of the brain (a semisolid non fixed structure). This information may be compared with CT or MRI data to again confirm the position of the brain relative to imaging data.

Making the focal point of the scope apparent to the operator is a problem solved by the present invention. Small neon lasers intended for use during presentations are utilized. Two of these lasers are aimed and focused at the focal point of the scope which would represent the point of reference in the stereotactic coordinate system. An added side effect to this solution is that the position above or below the target can be known in terms of the focal point by noting whether one or two laser points are visible.

A computer oriented stereotactic microneurological surgery apparatus includes an operating instrument having an operating axis. First and second extensions have proximal ends attached to the operating instrument. First and second focused energy sources connected to distal ends of the first and second. extensions respectively have first and second energy axes. The first and second energy sources positioned on the distal ends of the extensions direct the first and second energy axes to intersect at a point spaced from the operating instrument.

The first and second energy sources are positioned so that the first and second energy axes intersect on the operating axis of the operating instrument.

Preferably an operating microscope has a focal point along an optical axis, and the first and second energy sources are positioned so that the energy beams intersect at the focal point of the operating microscope.

In preferred embodiments, the first and second energy sources are first and second neon lasers which produce narrow beams along their energy axes, and which produce spots upon contacting tissue along the energy axes.

Preferably the spots of the first and second lasers coincide at a focal point of the operating microscope along the optical axis.

In a preferred embodiment, a position sensor is connected to the operating microscope for sensing position of the operating microscope.

Preferably the sensor senses positional changes.

A preferred sensor is a gyroscopic sensor.

Preferably the gyroscopic sensor comprises a gyroscope mounted on the operating microscope.

The preferred gyroscopic sensor comprises first and second gyroscopes mounted on the operating microscope.

Computer oriented stereotactic microneurological surgery apparatus is provided for an operating microscope. A movable positionable support has a distal end connected to an operating microscope and a proximal end connected to a fixed support. A gyroscopic position sensor on the microscope senses position of the microscope with respect to a fixed object.

One gyroscopic sensor includes a laser ring gyro connected to the operating microscope.

In one embodiment, the gyroscopic sensor comprises first and second gyroscopes connected to the operating microscope.

Preferably a processor is connected to the gyroscopes for indicating spatial position of the gyroscopes and spatial position of the operating microscope.

One embodiment includes a positional corrector connected to the processor for determining position of the focal point on the optical axis of the operating microscope.

An operating microscope has extensions on which are mounted neon lasers which focus beams through the focal point on the optical axis of the operating microscope. The beams produce two spots on an object when the object is away from the focal point, and a single spot on an object at a the focal point. Lightweight laser ring gyroscopes are connected to the operating microscope to determine spatial changes in the position and direction of the operating microscope and the focal point of the microscope.

These and further and other objects and features of the invention are apparent in the disclosure, which includes the above and ongoing written specification, with the claims and the drawings.

DETAILED DESCRIPTION OF THE DRAWINGS

Figure 1:
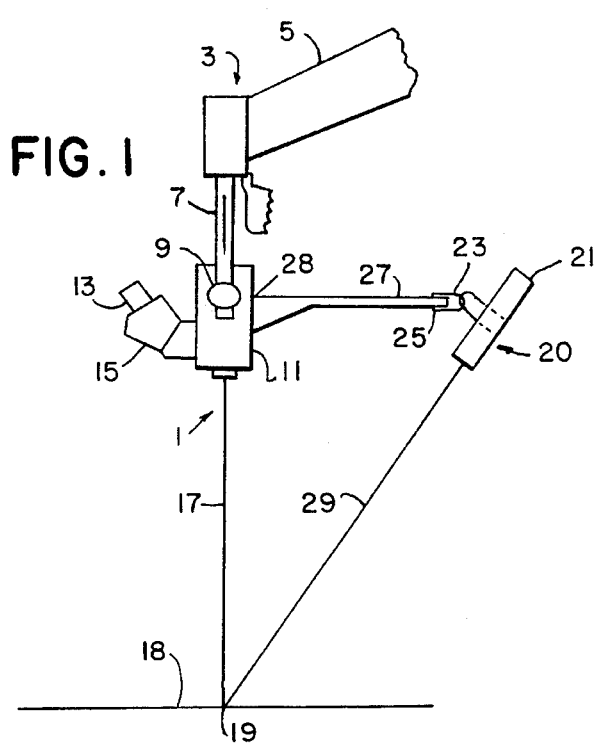
FIG. 1 is a side elevation of an operating microscope according to the present invention.

Referring to FIG. 1, an operating microscope generally indicated by the numeral 1 has a support 3 with an arm 5 pivoted from a fixed point. An adjustment 7 and a securable pivot 9 fix the position of a chamber 11, which includes optics. An eye piece 13 extends from angled housing 15, which contains prisms. The operating microscope has an optical axis 17 and a focal plane 18, which intersects the optical axis at a focal point 19. The invention provides a spot-creating laser apparatus generally indicated by the numeral 20. A neon laser 21 is supported on a movable and fixable pivot 23 on the distal end 25 of an extension 27. The proximal end 28 of the extension is fixed to the main operating microscope housing 11. The neon laser 21 produces a thin pencil beam 29 along its energy axis. The beam 29 intersects the optical axis 17 at the focal point 19 of the operating microscope 1.

Figure 2:
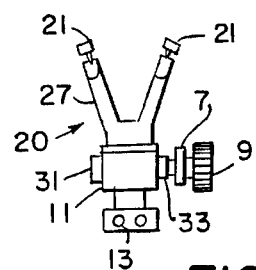
FIG. 2 is a plan view of the operating microscope shown in FIG. 1.

As shown in FIG. 2, the laser system comprises two lasers 21, each of which produces a beam. The position of the operating microscope body on the vertical supports 7 is adjustable by turning the adjustment 9. Two oculars 13 are used for binocular stereoscopic vision.

Figure 3:
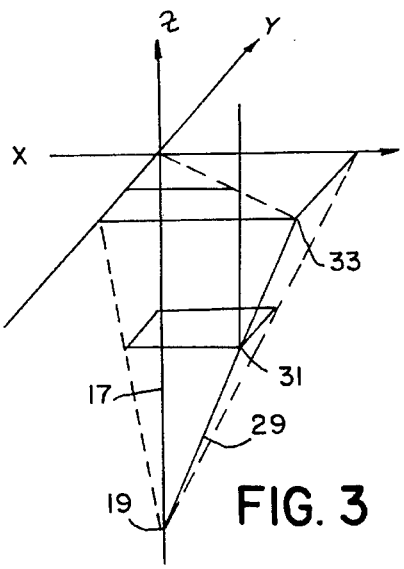
FIG. 3 is a schematic detail of the relation between geometric elements of the invention.

As shown in FIG. 3, the focal point 19 is the same as the coincident point of the optical axis 17 and the energy axis. Two gyroscopes 31 and 33 are positioned at different positions on the operating microscope body 11. The first gyroscope is positioned at X1, Y1, Z1, and the second gyroscope 33 is positioned at X2, Y2, Z2.

A represents the angular deviation from the orthogonal in the XY plane, and B represents the angular deviation from the orthogonal axes in the Y plane.

$$A = ACS \frac{|X1 - X2|}{LB}$$

$$B = ACS \frac{|Y1 - Y2|}{LB}$$

LB is the positional difference between gyroscope 31 and gyroscope 33.

Figure 4:
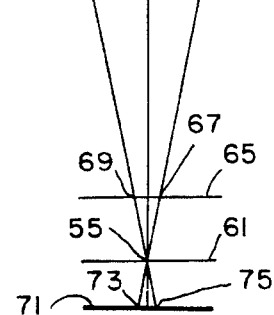
FIG. 4 is a schematic representation of the present invention.
Figure 4A:
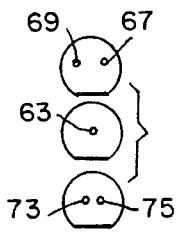
FIG. 4A shows views through an operating microscope.

Referring to FIG. 4, an operating instrument 40, which may be an operating microscope or any other operating instrument such as, for example, transcranial dopplers or linear accelerators or any other types of instruments, has a body 41 attached to a support (not shown). Extensions 43 are connected to the body 41 and have pivots 45 at opposite ends for supporting focused energy sources 47 and 49. The focused energy sources may produce invisible beams 51 and 53 which are capable of illuminating an object. The beams may have different frequencies or colors. Laser beams are preferred. Another example of an energy source might be a focused flashlight producing a thin light beam. The beams 51 and 53 converge at a point 55 along an operating axis 57 of the instrument 40. When the beams converge in a single point on a target 61, a single spot 63 appears as shown in the central view of the three views of FIG. 4A.

When an object 65 is too close, two spots 67 and 69 appear from the beams 51 and 53 respectively. When the object 71 is too far, two spots 73 and 75 appear respectively.

In the case of an operating microscope used, for example, while surgically creating a pathway to a desired site, one may use the two spots 67 and 69 to show extremities of the desired cut to reach the object point 55, which would be indicated by the single spot 63. The operating microscope may then be advanced towards the subject to create two more dots to delineate the next passageway to the desired target single spot. In some cases, as for example, brain surgery, the tissue may be mechanically separated or urged apart along natural cleavage lines.

Figure 5:
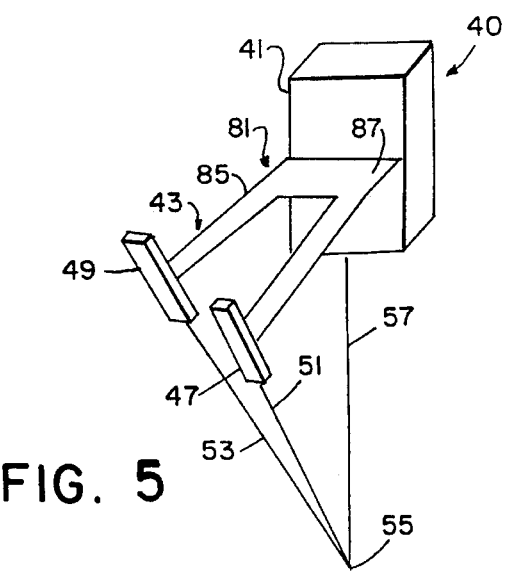
FIG. 5 is a schematic representation of a form of the invention.
Figure 6:
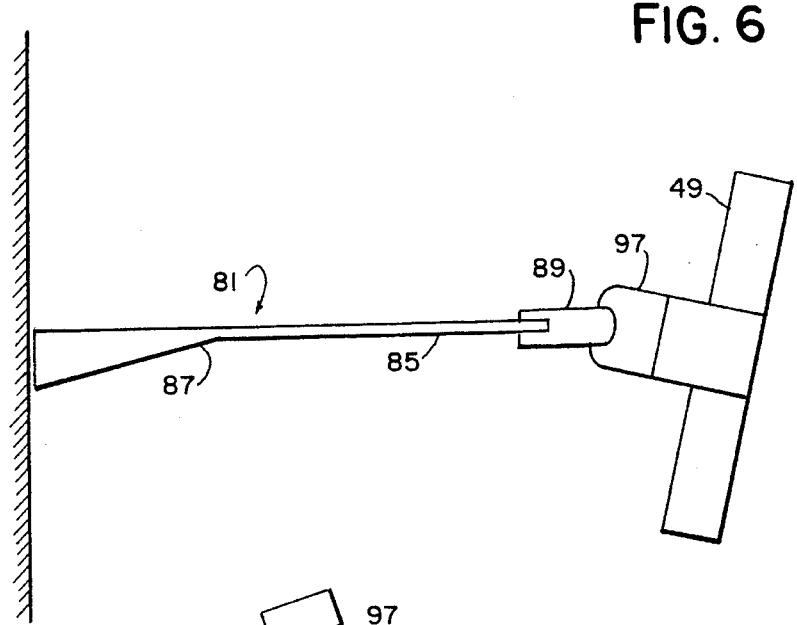
FIG. 6 is an enlarged detail of elements shown in FIG. 5.
Figure 7:
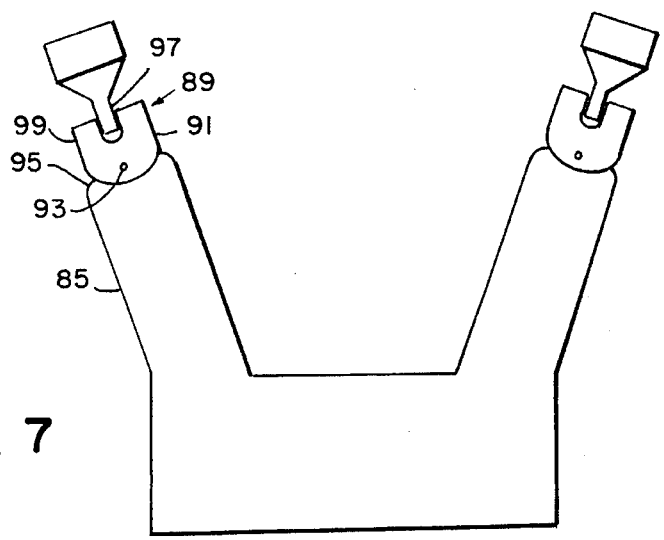
FIG. 7 is a further schematic representation of elements shown in FIGS. 5 and 6.

FIG. 5 is a perspective schematic view of the instrument 40 shown in FIG. 4. The extensions 43 are part of a U-shaped attachment 81 which has legs 83 and 85 for supporting individual laser sources 47 and 49. As shown in the side view of FIG. 6, the supporting bracket 81 has a tapering base portion 87 and a thin outward arm 85 with a pivot 89 mounted at the outer extension of the arm to allow adjustment of the laser 49 to a fixed predetermined position. A plan view of the support shown in FIGS. 5 and 6 is shown in FIG. 7. The universal joint 89 has a first clevis 91 connected to a first pin 93 on the distal end 95 of arm 85. A second portion 97 of the universal joint is connected to the ends of the clevis by pin 99. The accuracy of the laser beams is tested, the laser beams, preferably neon lasers, are adjusted by adjusting the universal joints 89, and then the joints are locked into the preferred position.

Figure 8:
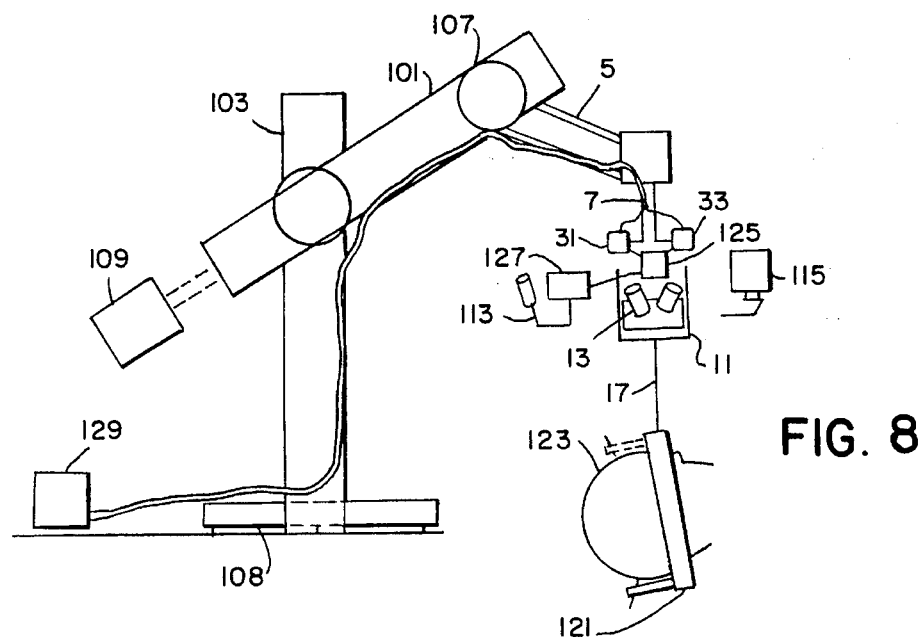
FIG. 8 is an overall schematic diagram of the apparatus.

Referring to FIG. 8, an operating microscope 11 is supported on a post 7, which is supported on an arm 5. A counterbalanced arm 101 is connected to a vertical stanchion 103 with a magnetic lock 105. A magnetic lock 107 connects the counterbalanced arm 101 to the support arm 105. A counterbalance 109 counterbalances the entire cantilevered assembly of the support arm 5 of the post 7 in the operating microscope 11 and attachments. The stanchion 103 is supported on legs 108. The operating microscope 11 may have accessory connections 111, such as for an associate's microscope 113 or a camera 115 which look along the optical axis 17 through beam splitters. Gyroscopes 31 and 33, preferably laser ring gyros, are connected to the instrument body and relay positional information as to the precise location of the instrument with a fixed member, such as a particular position on the stereotactic frame 121 attached to the patient's skull 123. As the operating microscope 11 is moved, the gyroscopes relay movement-related positional information. In one simple form, the gyroscopes may be connected to small outputs 125, functioning as positional corrector means, on the operating microscope, which in turn convey information to heads-up displays 127, which provide information through beam splitters to the field of vision within the operating microscope. Preferably the gyroscopes 31 and 33, or a single gyroscope, are connected through wires passing along the arms 5 and 101 to a processor 129, which translates the information received from the gyroscopes into the focal point position in the stereotactic coordinate system. That positional information may be related to a heads-up display within the microscope.

In alternate forms of the invention, the positional information from the processor 129 may be related to positional information from previous scans, and servomotors may move the arms 101 and 5 to precisely position the operating microscope 111 for optical guidance of hand-held instruments through predetermined access pathways to objective points within the brain.

The system of the present invention has equal application to operating microscopes, linear accelerators, transcranial dopplers, or open cranial 2D dopplers, or any other systems which require or advantageously use precise positional information.

While the invention has been described with reference to specific embodiments, modifications and variations of the invention may be constructed without departing from the scope of the invention, which is defined in the following claims.

I claim:

1. A computer oriented stereotactic microneurological surgery apparatus, comprising an operating instrument, first and second extensions having proximal ends attached to the operating instrument and having distal ends, first and second energy sources connected to distal ends of the first and second extensions respectively and having first and second energy beams, the first and second energy sources being positioned on the distal ends of the extensions so as to direct the first and second energy beams to intersect at a point spaced from the operating instrument, wherein the first and second energy sources are positioned so that the first and second energy beams intersect on an operating axis of the operating instrument, wherein the operating instrument is an operating microscope and the operating axis is an optical axis and a focal point is along the optical axis, and wherein the first and second energy sources are positioned so that the energy beams intersect at the focal point of the operating microscope, wherein the first and second energy sources are first and second neon lasers which produce narrow beams along the optical axis, and which produce spots upon contacting tissue along the optical axis.

2. A computer oriented stereotactic microneurological surgery apparatus, comprising an operating instrument, first and second extensions having proximal ends attached to the operating instrument and having distal ends, first and second energy sources connected to distal ends of the first and second extensions respectively and having first and second energy beams, the first and second energy sources being positioned on the distal ends of the extensions so as to direct the first and second energy beams to intersect at a point spaced from the operating instrument, wherein the first and second energy sources are positioned so that the first and second energy beams intersect on an operating axis of the operating instrument, wherein the operating instrument is an operating microscope and the operating axis is an optical axis and a focal point is along the optical axis, and wherein the first and second energy sources are positioned so that the energy beams intersect at the focal point of the operating microscope, wherein the beams of the first and second lasers coincide at a focal point of the operating microscope along the optical axis.

3. A computer oriented stereotactic microneurological surgery apparatus, comprising an operating instrument, first and second extensions having proximal ends attached to the operating instrument and having distal ends first and second energy sources connected to distal ends of the first and second extensions respectively and having first and second energy beams, the first and second energy sources being positioned on the distal ends of the extensions so as to direct the first and second energy beams to intersect at a point spaced from the operating instrument, further comprising a position sensor connected to the operating instrument and a processing means for sensing position of the operating instrument.

4. The apparatus of claim 3, wherein the sensor senses positional changes.

5. The apparatus of claim 4, wherein the sensor is a gyroscopic sensor.

6. The apparatus of claim 5, wherein the gyroscopic sensor comprises a gyroscope mounted on the operating instrument.

7. The apparatus of claim 5, wherein the gyroscopic sensor comprises first and second gyroscopes mounted on the operating instrument.

8. A computer oriented stereotactic microneurological surgery apparatus, comprising an operating instrument, first and second energy sources connected to the operating instrument, a positionable support having a distal end connected to the operating instrument and having a proximal end connected to a fixed support, a gyroscopic position sensor on the instrument for sensing position of the instrument with respect to a fixed object, a processing means connected to the sensor for processing the sensed position of the instrument.

9. The apparatus of claim 8, further comprising first and second extensions having proximal ends attached to the operating instrument and having distal ends, the first and second energy sources being connected to distal ends of the first and second extensions respectively and having first and second energy beams, the first and second energy sources being positioned on the distal ends of the extensions so as to direct the first and second energy beams to intersect at a point spaced from the operating instrument.

10. The apparatus of claim 9, wherein the first and second energy sources are positioned so that the first and second energy beams intersect on an operating axis of the operating instrument.

11. The apparatus of claim 10, wherein the operating instrument is an operating microscope which has an optical axis and a focal point along the optical axis, and wherein the first and second energy sources are positioned so that the energy beams intersect at the focal point of the operating microscope.

12. The apparatus of claim 8, wherein the gyroscopic sensor comprises a laser ring gyro connected to the operating instrument.

13. The apparatus of claim 8, wherein the gyroscopic sensor comprises first and second gyroscopes connected to the operating instrument.

14. The apparatus of claim 13, wherein the processing means connected to the gyroscopes is for indicating spatial position of the gyroscopes and spatial position of the operating instrument.

15. The apparatus of claim 14, wherein the operating instrument is an operating microscope having an optical axis and a focal point along the optical axis.

16. The apparatus of claim 15, further comprising a positional corrector means connected to the processor for determining position of the focal point on the optical axis of the operating microscope.

* * * * *